(12) United States Patent
Taff et al.

(10) Patent No.: US 11,311,332 B2
(45) Date of Patent: *Apr. 26, 2022

(54) THROMBECTOMY DEVICES

(71) Applicants: Yuval Taff, Tel Aviv (IL); Gal Stern, Tel Aviv (IL); Itzhak Orion, Beer Sheva (IL)

(72) Inventors: Yuval Taff, Tel Aviv (IL); Gal Stern, Tel Aviv (IL); Itzhak Orion, Beer Sheva (IL)

(73) Assignee: MAGNETO THROMBECTOMY SOLUTIONS LTD., Or Yehuda (IL)

( * ) Notice: Subject to any disclaimer, the term of this patent is extended or adjusted under 35 U.S.C. 154(b) by 944 days.

This patent is subject to a terminal disclaimer.

(21) Appl. No.: 15/859,776

(22) Filed: Jan. 2, 2018

(65) Prior Publication Data

US 2018/0116717 A1    May 3, 2018

Related U.S. Application Data

(63) Continuation-in-part of application No. 13/127,118, filed on Aug. 23, 2011, now Pat. No. 10,028,782.

(Continued)

(51) Int. Cl.
*A61B 18/14* (2006.01)
*A61B 18/00* (2006.01)
*A61B 17/22* (2006.01)

(52) U.S. Cl.
CPC ............ *A61B 18/1492* (2013.01); *A61B 2017/22068* (2013.01); *A61B 2018/0022* (2013.01);

(Continued)

(58) Field of Classification Search
CPC .......... A61B 18/18; A61B 2018/00071; A61B 2018/00077; A61B 2018/0022;
(Continued)

(56) References Cited

U.S. PATENT DOCUMENTS 4,027,674 A    6/1977 Tessler et al.
4,682,596 A    7/1987 Bales et al.
(Continued)

FOREIGN PATENT DOCUMENTS

DE    102010014778 A1    10/2011
EP    1980200 A2    10/2008
(Continued)

OTHER PUBLICATIONS

International Application PCT/IB2019/055032 Search Report dated Oct. 28, 2019.

(Continued)

*Primary Examiner* — Eun Hwa Kim
(74) *Attorney, Agent, or Firm* — Kligler & Associates Patent Attorneys Ltd

(57) ABSTRACT

Described embodiments include an apparatus for removal of a thrombus from a body of a subject. The apparatus includes a first electrode, made of a first conductive metal, a second electrode, made of a second conductive metal that is different from the first conductive metal, and a voltage source, configured to apply a positive unipolar voltage between the first electrode and the second electrode while the first electrode is in contact with the thrombus, and while the second electrode is inside the body of the subject. Other embodiments are also described.

21 Claims, 3 Drawing Sheets

Related U.S. Application Data

(60) Provisional application No. 62/519,185, filed on Jun. 14, 2017, provisional application No. 62/442,470, filed on Jan. 5, 2017.

(52) U.S. Cl.
CPC .............. *A61B 2018/0041* (2013.01); *A61B 2018/00077* (2013.01); *A61B 2018/00083* (2013.01); *A61B 2018/00767* (2013.01); *A61B 2018/00875* (2013.01); *A61B 2018/1435* (2013.01)

(58) Field of Classification Search
CPC .. A61B 2018/00398; A61B 2018/0041; A61B 2018/00416; A61B 2018/00422; A61B 2018/00428; A61B 2018/00571; A61B 2018/00625; A61B 2018/00892; A61B 2018/126; A61B 2018/1266
See application file for complete search history.

(56) References Cited

U.S. PATENT DOCUMENTS

| | | | |
|---|---|---|---|
| 5,122,136 A | 2/1992 | Guglielmi | |
| 5,125,928 A | 6/1992 | Parins et al. | |
| 5,300,068 A * | 4/1994 | Rosar | A61B 18/1492 606/32 |
| 5,433,708 A | 7/1995 | Nichols et al. | |
| 5,449,357 A | 9/1995 | Zinnanti | |
| 5,507,743 A | 4/1996 | Edwards et al. | |
| 5,569,204 A | 10/1996 | Cramer | |
| 5,603,731 A | 2/1997 | Whitney | |
| 5,827,278 A | 10/1998 | Webster | |
| 5,851,206 A | 12/1998 | Guglielmi et al. | |
| 5,876,398 A | 3/1999 | Mulier et al. | |
| 5,913,854 A | 6/1999 | Maguire et al. | |
| 5,925,042 A | 7/1999 | Gough et al. | |
| 6,047,700 A | 4/2000 | Eggers et al. | |
| 6,179,824 B1 | 1/2001 | Eggers et al. | |
| 6,210,404 B1 | 4/2001 | Shadduck | |
| 6,248,113 B1 | 6/2001 | Fina | |
| 6,322,559 B1 | 11/2001 | Daulton et al. | |
| 6,554,827 B2 | 4/2003 | Chandrasekaran et al. | |
| 6,658,288 B1 | 12/2003 | Hayashi | |
| 6,730,104 B1 | 5/2004 | Sepetka et al. | |
| 6,855,143 B2 | 2/2005 | Davison et al. | |
| 8,197,478 B2 | 6/2012 | Hayashi et al. | |
| 8,473,029 B2 | 6/2013 | Gerhart et al. | |
| 8,579,893 B2 | 11/2013 | Hoey | |
| 8,747,416 B2 | 6/2014 | Hakala et al. | |
| 8,814,859 B2 | 8/2014 | Drasler et al. | |
| 8,968,304 B2 | 3/2015 | Katou | |
| 10,434,295 B2 | 10/2019 | Stigall et al. | |
| 10,758,303 B2 | 9/2020 | Xiao et al. | |
| 2001/0001314 A1* | 5/2001 | Davison | A61B 18/1492 606/41 |
| 2002/0058937 A1 | 5/2002 | Maltese et al. | |
| 2002/0072740 A1* | 6/2002 | Chandrasekaran | A61B 18/1492 606/41 |
| 2002/0072764 A1 | 6/2002 | Sepetka et al. | |
| 2002/0133111 A1 | 9/2002 | Shadduck | |
| 2003/0050634 A1 | 3/2003 | Ellman et al. | |
| 2003/0125787 A1 | 7/2003 | Shcherinsky | |
| 2003/0130571 A1 | 7/2003 | Lattouf | |
| 2004/0073243 A1* | 4/2004 | Sepetka | A61M 25/0082 606/159 |
| 2004/0082948 A1 | 4/2004 | Stewart et al. | |
| 2005/0159739 A1 | 7/2005 | Paul et al. | |
| 2005/0251134 A1* | 11/2005 | Woloszko | A61B 18/149 606/46 |
| 2006/0089638 A1 | 4/2006 | Carmel et al. | |
| 2006/0195137 A1 | 8/2006 | Sepetka et al. | |
| 2006/0224155 A1* | 10/2006 | Schmaltz | A61B 18/1492 606/41 |
| 2007/0027448 A1 | 2/2007 | Paul et al. | |
| 2007/0078457 A1 | 4/2007 | Paul et al. | |
| 2007/0156082 A1 | 7/2007 | Scherman | |
| 2007/0156130 A1* | 7/2007 | Thistle | A61B 18/1477 606/41 |
| 2007/0255270 A1 | 11/2007 | Carney | |
| 2008/0161796 A1 | 7/2008 | Cao et al. | |
| 2008/0161803 A1 | 7/2008 | Oral et al. | |
| 2008/0161893 A1 | 7/2008 | Paul et al. | |
| 2008/0262489 A1* | 10/2008 | Steinke | A61B 18/1492 606/33 |
| 2011/0022045 A1 | 1/2011 | Cao et al. | |
| 2011/0301594 A1 | 12/2011 | Orion | |
| 2011/0308527 A1 | 12/2011 | Harrington et al. | |
| 2012/0130169 A1 | 5/2012 | Mesallum | |
| 2012/0232374 A1 | 9/2012 | Werneth et al. | |
| 2012/0239022 A1 | 9/2012 | Wolfe | |
| 2012/0296262 A1 | 11/2012 | Ogata et al. | |
| 2013/0090644 A1 | 4/2013 | Williams | |
| 2013/0123872 A1 | 5/2013 | Bomzin et al. | |
| 2013/0325003 A1 | 12/2013 | Kapur et al. | |
| 2014/0074113 A1 | 3/2014 | Hakala et al. | |
| 2014/0276748 A1 | 9/2014 | Ku et al. | |
| 2014/0277013 A1 | 9/2014 | Sepetka et al. | |
| 2014/0309579 A1 | 10/2014 | Rubinsky et al. | |
| 2014/0364896 A1 | 12/2014 | Consigny | |
| 2015/0038963 A1 | 2/2015 | Panos et al. | |
| 2015/0133990 A1 | 5/2015 | Davidson | |
| 2016/0066989 A1 | 3/2016 | Davies et al. | |
| 2018/0161085 A1 | 6/2018 | Shin et al. | |

FOREIGN PATENT DOCUMENTS

| | | | |
|---|---|---|---|
| EP | 2359764 | A1 | 8/2011 |
| WO | 9426228 | A1 | 11/1994 |
| WO | 9724993 | A1 | 7/1997 |
| WO | 0062851 | A1 | 10/2000 |
| WO | 0124720 | A1 | 4/2001 |
| WO | 2014025397 | A1 | 2/2014 |
| WO | 2014151123 | A1 | 9/2014 |
| WO | 2015074032 | A1 | 5/2015 |
| WO | 2015076864 | A1 | 5/2015 |
| WO | 2018172891 | A1 | 9/2018 |
| WO | 2019243992 | A1 | 12/2019 |

OTHER PUBLICATIONS

International Application PCT/IB2018/050010 Search Report dated May 10, 2018.
International Application PCT/IB2018/051731 Search Report dated Jul. 5, 2018.
International Application PCT/IB2018/058946 Search Report dated Feb. 21, 2019.
Australian application # 2018206023 office action dated May 8, 2020.
European Application # 18736539.0 search report dated Jul. 3, 2020.
European Application # 18772459.6 search report dated Jul. 10, 2020.
International Application # PCT/IB2020/051418 search report dated May 31, 2020.
Sawyer et al., "Electrical Hemostasis in Uncontrollable Bleeding States", Annais of Surgery , vol. 154, Issue 4, pp. 556-562, Oct. 1961.
Gralla et al., "A dedicated animal model for mechanical thrombectomy in acute stroke", American Journal of Neuroradiology, vol. 27, Issue 6, pp. 1357-1361, Jun.-Jul. 2006.
EP Application # 18880491.8 Search Report dated Jun. 23, 2021.
CN Application # 2018800054493 Office Action dated Jun. 2, 2021.
JP Application # 2019546193 Office Action dated Oct. 26, 2021.
JP Application # 2019531818 Office Action dated Nov. 2, 2021.
CN Application #2018800054493 Office Action dated Nov. 9, 2021.
U.S. Appl. No. 16/381,014 Office Action dated Dec. 7, 2021.

(56) References Cited

OTHER PUBLICATIONS

International Application # PCT/IB2021058330 Search Report dated Jan. 12, 2022.
CN Application #201880017216.5 Office Action dated Dec. 9, 2021.
EP Application # 18880491.8 Office Action dated Feb. 10, 2022.
U.S. Appl. No. 16/381,014 Office Action dated Feb. 17, 2022.
EP Application # 119823746.3 Search Report dated Mar. 4, 2022.

* cited by examiner

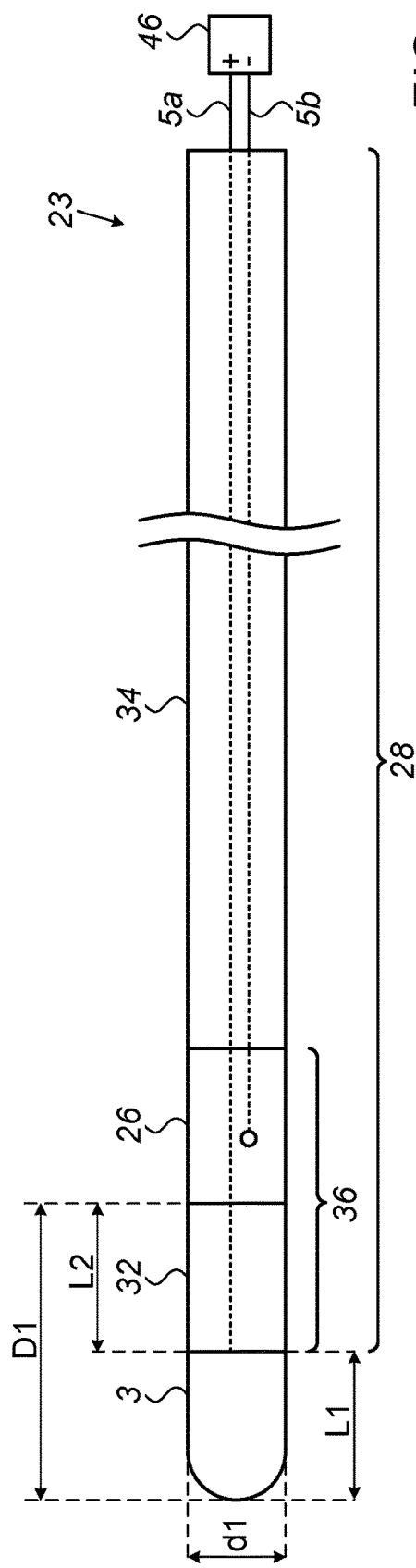
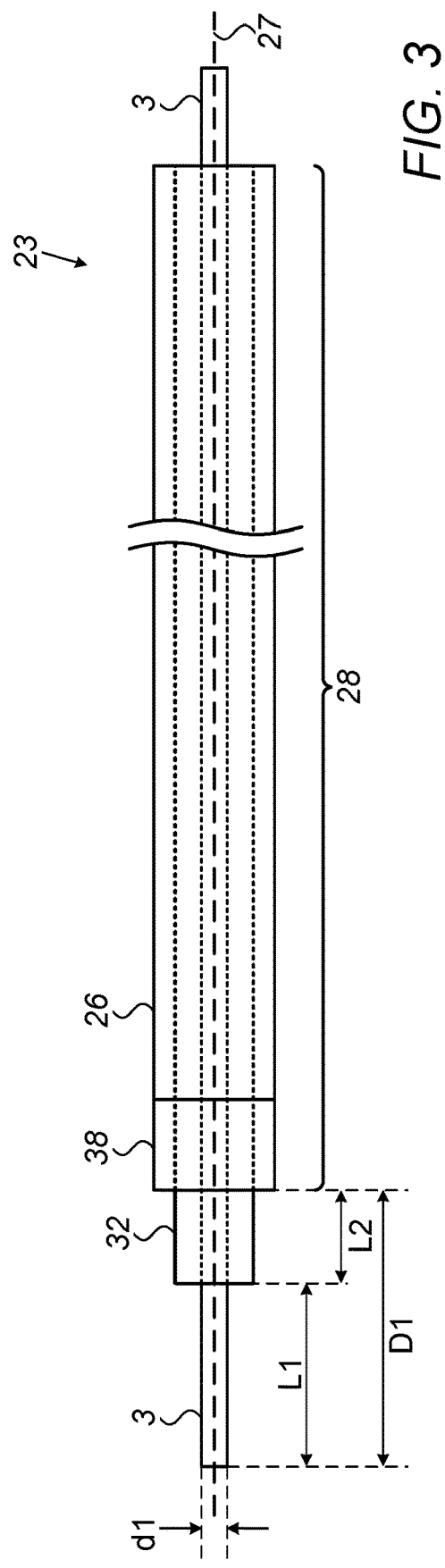

THROMBECTOMY DEVICES

CROSS-REFERENCE TO RELATED APPLICATIONS

The present application is a continuation-in-part of, and claims the benefit of, U.S. patent application Ser. No. 13/127,118, published as US Patent Application Publication 2011/0301594, entitled "Method and apparatus for thrombus dissolution/thrombectomy by an electrode catheter device," whose disclosure is incorporated herein by reference. The present application also claims the benefit of (i) U.S. Provisional Application 62/442,470, entitled "Thrombectomy device," filed Jan. 5, 2017, and (ii) US Provisional Application 62/519,185, entitled "Electric thrombectomy device," filed Jun. 14, 2017, the disclosures of which are incorporated herein by reference. The present application is also related to an international patent application, entitled "Thrombectomy devices," filed on even date herewith.

FIELD OF THE INVENTION

The present application relates to the field of medical devices, particularly devices for thrombectomy, i.e., the removal of thrombi (blockages) from blood vessels.

BACKGROUND

US Patent Application Publication 2004/0073243 describes devices and methods for removing an obstruction from a blood vessel. The devices are deployed in a collapsed condition and are then expanded within the body. The devices are then manipulated to engage and remove the obstruction.

U.S. Pat. No. 6,855,143 describes electrosurgical apparatus and methods for maintaining patency in body passages subject to occlusion by invasive tissue growth. The apparatus includes an electrode support disposed at a shaft distal end having at least one active electrode arranged thereon, and at least one return electrode proximal to the at least one active electrode. In one embodiment, a plurality of active electrodes each comprising a curved wire loop portion are sealed within a distal portion of the electrode support.

U.S. Pat. No. 8,197,478 describes an apparatus and method for electrically induced thrombosis. The surgical device includes a first electrode and a second electrode. The first electrode is for placement adjacent to, near, or within a treatment site of a patient. The second electrode can be movable with respect to the first electrode. When the electrodes are charged by an electricity source, negatively charged blood components are attracted to the positively charged electrode while being repelled from the negatively charged electrode. Due to the electric potential between the adjacent electrodes, thrombosis is induced. The negatively charged blood and components form a thrombus or a clot adjacent to the positively charged electrode. The surgical device can be used to induce the otherwise natural process of thrombosis. When the surgical device is used in a treatment site such as a puncture or incision, the thrombosis can seal the opening created by the treatment site.

US Patent Application Publication 2002/0133111 describes a microcatheter for removing thromboemboli from cerebral arteries in patients suffering from ischemic stroke. The microcatheter provides an extraction lumen that can be scaled to a very small diameter that is still capable of extracting and emulsifying thrombus without clogging the channel. The microcatheter uses a series of spaced apart energy application mechanisms along the entire length of the catheter's extraction lumen to develop sequential pressure differentials to cause fluid flows by means of cavitation, and to contemporaneously ablate embolic materials drawn through the extraction lumen by cavitation to thereby preventing clogging of the lumen. Preferred mechanisms for energy delivery are (i) a laser source and controller coupled to optic fibers in the catheter wall or (ii) an Rf source coupled to paired electrodes within the extraction lumen. Each energy emitter can apply energy to fluid media in the extraction channel of the catheter—wherein the intense energy pulses can be sequentially timed to cause fluid media flows in the proximal direction in the channel.

SUMMARY OF THE INVENTION

There is provided, in accordance with some embodiments of the present invention, apparatus for removal of a thrombus from a body of a subject. The apparatus includes a first electrode, made of a first conductive metal, a second electrode, made of a second conductive metal that is different from the first conductive metal, and a voltage source, configured to apply a positive unipolar voltage between the first electrode and the second electrode while the first electrode is in contact with the thrombus, and while the second electrode is inside the body of the subject.

In some embodiments, an electronegativity of the first conductive metal is greater than an electronegativity of the second conductive metal.

In some embodiments, a distance between the first electrode and the second electrode is less than 3 mm.

In some embodiments, the distance is less than 0.7 mm.

In some embodiments, the apparatus further includes a tube, and the second electrode is shaped to define at least part of a wall of the tube.

In some embodiments, the first electrode is disposed at a distal end of the tube.

In some embodiments, the first electrode passes through a lumen of the tube.

In some embodiments, the second electrode is shaped to define a helix, and the first electrode passes through the second electrode.

In some embodiments, the first electrode and second electrode are coaxial with one another.

In some embodiments, a length of an exposed portion of the first electrode is between 0.1 and 50 mm.

In some embodiments, a diameter of the first electrode is between 0.01 and 4 mm.

In some embodiments, an amplitude of the unipolar voltage is between 1 and 100 V.

In some embodiments, in applying the unipolar voltage, the voltage source is configured to pass, between the first electrode and the second electrode, a current having an amplitude of between 0.1 and 4 mA.

In some embodiments, the first electrode includes a straight distal end.

In some embodiments, the apparatus further includes a balloon proximal to the first electrode, configured to center the first electrode with respect to the thrombus when inflated.

There is further provided, in accordance with some embodiments of the present invention, a method that includes applying a positive unipolar voltage between a first electrode, made of a first conductive metal, and a second electrode, made of a second conductive metal that is different from the first conductive metal, while the first electrode is in contact with a thrombus in a body of a subject, and while the second electrode is inside the body of the subject. The method further includes, subsequently, removing the thrombus from the body of the subject.

In some embodiments, the method further includes, prior to applying the unipolar voltage, advancing the first electrode through the thrombus, at least until the thrombus contacts an electrical insulator that is disposed proximally to an exposed portion of the first electrode.

In some embodiments, the method further includes measuring an impedance between the first electrode and the second electrode, and ascertaining that the thrombus has contacted the insulator, based on the measured impedance.

In some embodiments, the method further includes, prior to applying the unipolar voltage, advancing the first electrode through the thrombus until an entire length of the first electrode contacts the thrombus.

In some embodiments, applying the unipolar voltage includes applying the unipolar voltage while a distance between a distal tip of the first electrode and a distal tip of the second electrode is between 1 and 100 mm.

In some embodiments, an electrical insulator is disposed proximally to an exposed portion of the first electrode, and the method further includes, prior to applying the unipolar voltage, advancing the second electrode over the insulator.

In some embodiments, the second electrode is expandable, and the method further includes, prior to applying the unipolar voltage:

advancing a catheter, containing both the first electrode, and the second electrode in a crimped position, through the thrombus; and subsequently, withdrawing the catheter, such that the second electrode expands, from the crimped position, within the thrombus.

In some embodiments, the method further includes, prior to contacting the thrombus with the first electrode, centering the first electrode with respect to the thrombus, by inflating a balloon that is proximal to the first electrode.

There is further provided, in accordance with some embodiments of the present invention, apparatus for removal of a thrombus from a body of a subject. The apparatus includes an outer electrode, shaped to define a helix, and an inner electrode, passing through the outer electrode, configured to attach to the thrombus when a positive unipolar voltage is applied between the inner electrode and the outer electrode.

In some embodiments, the outer electrode is expandable.

In some embodiments, the apparatus further includes a voltage source configured to apply the positive unipolar voltage.

In some embodiments, the apparatus further includes an electrically-insulating cover over both a proximal portion of the outer electrode and a distal portion of the outer electrode.

In some embodiments, the inner electrode is rod-shaped.

In some embodiments, the inner electrode passes through a center of the outer electrode.

In some embodiments, a distance between the inner electrode and a middle portion of the outer electrode is between 1 and 100 mm.

In some embodiments, the distance is between 2 and 30 mm.

In some embodiments, the inner electrode is made of a first conductive metal having a first electronegativity, and the outer electrode is made of a second conductive metal having a second electronegativity that is less than the first electronegativity.

There is further provided, in accordance with some embodiments of the present invention, a method that includes advancing a catheter, which contains both a crimped outer electrode, and an inner electrode that passes through the outer electrode, through a thrombus in a body of a subject. The method further includes, subsequently to advancing the catheter through the thrombus, withdrawing the catheter, such that the outer electrode expands within the thrombus. The method further includes, subsequently to withdrawing the catheter, applying a positive unipolar voltage between the inner electrode and the outer electrode, such that the thrombus becomes attached to the inner electrode, and, subsequently to the thrombus becoming attached to the inner electrode, withdrawing the inner electrode and the outer electrode from the body of the subject.

In some embodiments, withdrawing the outer electrode includes, using the outer electrode, applying a mechanical force to the thrombus.

The present invention will be more fully understood from the following detailed description of embodiments thereof, taken together with the drawings, in which:

BRIEF DESCRIPTION OF THE DRAWINGS

FIGS. 2-4 are schematic illustrations of electrode assemblies, in accordance with some embodiments of the present invention.

DETAILED DESCRIPTION OF EMBODIMENTS

Overview

Embodiments of the present invention provide apparatus and methods for removing a thrombus from a blood vessel or other body passage, by application of a unipolar voltage between two electrodes in the body passage. For example, a positive unipolar voltage may be applied between a first electrode in contact with the thrombus, and a second electrode disposed proximally to the first electrode. The positive voltage causes the first electrode to attract the negatively-charged thrombus, such that the thrombus attaches to the first electrode. Subsequently, the thrombus may be removed by withdrawing the first electrode. Alternatively, a negative unipolar voltage may be applied between the first and second electrodes, causing dissolution of the thrombus. Subsequently, the disintegrated thrombus may be removed from the subject.

Advantageously, the electrodes may be made of different conductive metals having different respective electronegativities, such as to increase the effect of the applied unipolar voltage. For example, the first, thrombus-contacting electrode may have a higher electronegativity than that of the second electrode, such as to increase the attraction between the thrombus and the thrombus-contacting electrode.

In some embodiments, the thrombus-contacting electrode is advanced through the thrombus, at least until the thrombus contacts an electrical insulator that is disposed proximally to the exposed portion of the first electrode. This reduces, or eliminates, any exposed surface area of the electrode proximally to the thrombus, thus further increasing the effect of the applied unipolar voltage. To ascertain that the thrombus has contacted the insulator, the impedance between the first electrode and the second electrode may be measured, since the impedance between the electrodes changes as a function of the degree to which the electrode is covered by the thrombus.

In some embodiments, the second electrode is shaped to define a helix, and the first electrode passes through the helix. Advantageously, the helical second electrode helps withdraw the thrombus from the subject, by applying, to the thrombus, a mechanical force that complements the force of electrical attraction between the thrombus and the first electrode.

In general, in the context of the present application, including the claims, the term "unipolar voltage" may refer to any voltage signal that is mostly of a single polarity, even if the signal is not strictly unipolar. For example, a voltage signal that, during each five-minute interval of the signal, is positive for at least 80% of the interval, may be referred to as a positive unipolar voltage.

In general, in the context of the present application, including the claims, the term "thrombus" may refer to any combination of blood, fat, cholesterol, plaque, and/or foreign materials originating from outside the body, which may possess an electric charge.

Apparatus Description

Figure 1:
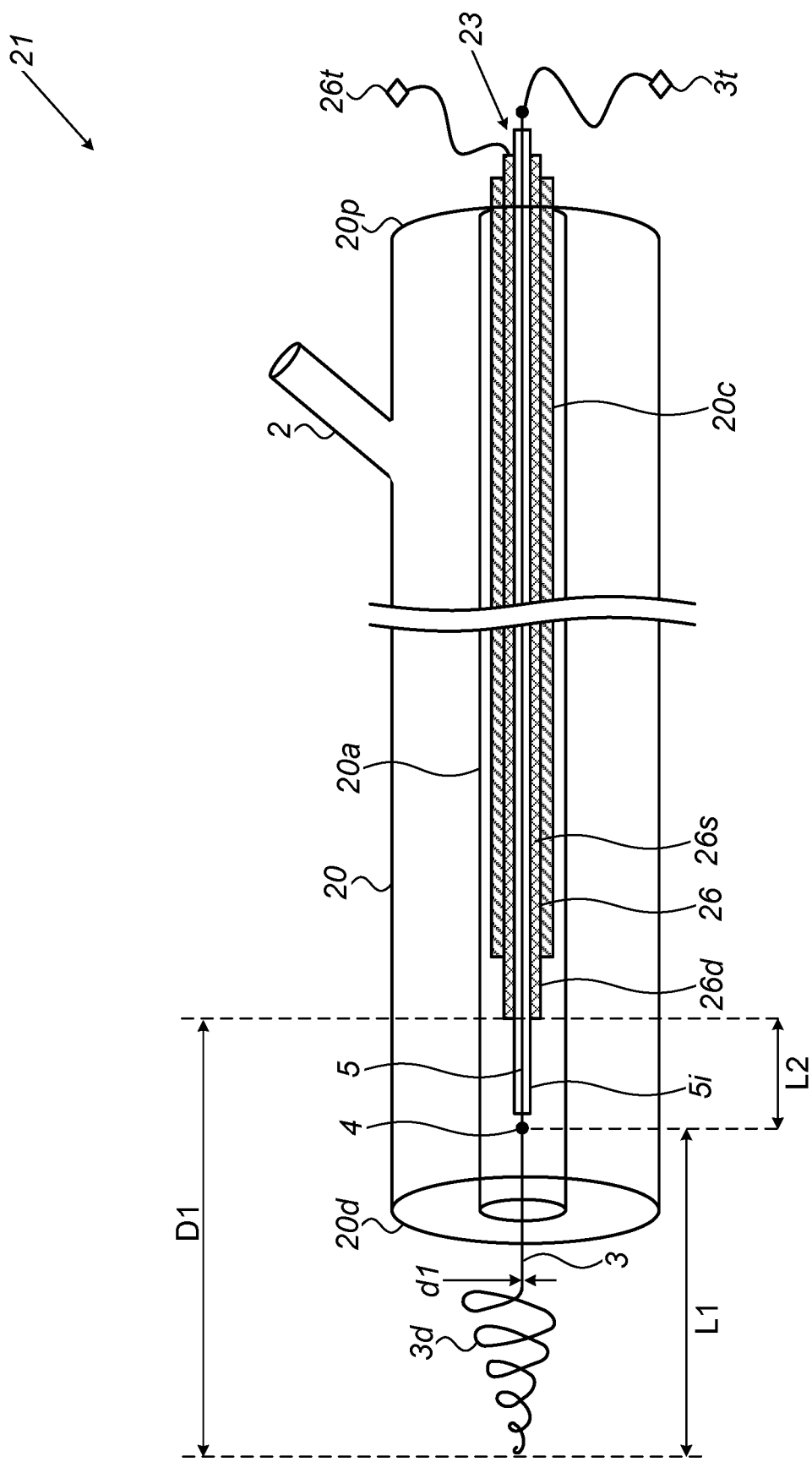
FIG. 1 is a schematic illustration of apparatus for removal of a thrombus from a body of subject, in accordance with some embodiments of the present invention.

Reference is initially made to FIG. 1, which is a schematic illustration of apparatus 21 for removal of a thrombus from a body of subject, in accordance with some embodiments of the present invention. (FIG. 1 generally corresponds to FIG. 2 of US Patent Application Publication 2011/0301594, whose disclosure is incorporated herein by reference.)

Apparatus 21 comprises a catheter 20, which has a proximal end 20p and a distal end 20d, and which is shaped to define a lumen 20a. Following the introduction of catheter 20 into the vascular system of the subject, e.g., using standard angiographic catheterization techniques, an electrode assembly is passed through lumen 20a, and is subsequently used to remove a thrombus from the vascular system, as described in detail hereinbelow. In some embodiments, catheter 20 further comprises a proximal, lateral port 2 for withdrawing any debris (e.g., thrombus fragments) generated during the treatment process, using a syringe (not shown) or any other device suitable for this purpose. Alternatively or additionally, a second catheter, passing over catheter 20, may be positioned proximally to the thrombus, and subsequently used to aspirate such debris. Alternatively or additionally, a net disposed near the distal end of electrode assembly 23 may be used to catch and remove such debris.

In the particular embodiment shown in FIG. 1, electrode assembly 23 comprises a pair of coaxial electrodes: a first electrode 3, which is used to contact the thrombus, and a second electrode 26. First electrode 3 comprises a wire having a diameter d1 that may have any suitable value, such as between 0.01 and 4 mm. First electrode 3 comprises a distal end 3d. In some embodiments, as shown in subsequent figures, distal end 3d is straight. Alternatively, as shown in FIG. 1, distal end 3d may be curly, or may have any other suitable shape that increases the contact area between the electrode and the thrombus, relative to a straight distal end. For example, the surface of distal end 3d (or of the entire first electrode) may comprise a plurality of protrusions, or bumps, which increase the surface area available for contact with the thrombus. Alternatively or additionally, distal end 3d (or the entire first electrode) may be curved, such as to decrease the likelihood that the electrode will damage tissue of the subject.

In some embodiments, first electrode 3 is connected at its proximal end, at a connection point 4, to another wire 5, which passes through lumen 20a to proximal end 20p of the catheter. In other embodiments, instead of wire 5, first electrode 3 extends through the lumen of the catheter, to the proximal end of the catheter.

Typically, an electrically-isolating material separates the first electrode from the second electrode, such that the first and second electrodes are electrically isolated from one another. For example, an electrically-isolating layer 5i may cover wire 5, with second electrode 26, in turn, covering electrically-isolating layer 5i. For example, as shown in FIG. 1, second electrode 26 may comprise a multi-stranded wire, comprising a plurality of electrically-conducting strands 26s that are braided over, or wrapped around, electrically-isolating layer 5i. In some embodiments, an electrically-isolating cover 20c covers most of the second electrode, such that only a distal portion 26d of the second electrode remains exposed. In some embodiments, distal portion 26d is between 7 and 25 mm long, e.g., around 15 mm long.

Typically, the first electrode—or the exposed portion of the first electrode, which is the portion of the first electrode not covered by electrically-isolating layer 5i—has a length L1 that is between 0.1 and 150 mm (e.g., between 5 and 50 mm, such as between 5 and 25 mm). Alternatively, length L1 may have any other suitable value. The distal end of the first electrode is typically blunt, to help prevent any damage to the lumen through which the first electrode is passed.

Wire 5 terminates, at its proximal end, at a first terminal 3t. Similarly, the second electrode terminates, at its proximal end, at a second terminal 26t. Upon the first electrode contacting the thrombus, a unipolar voltage is applied between the electrodes, via first terminal 3t and second terminal 26t. A positive unipolar voltage between the first and second electrodes facilitates a thrombectomy (i.e., a removal of the thrombus), by causing the negatively-charged thrombus to become attached to the first electrode. Such a positive voltage may be obtained, for example, by grounding second terminal 26t, while applying a positive unipolar voltage signal to first terminal 3t. Conversely, a negative unipolar voltage between the first and second electrodes facilitates dissolution of the thrombus. Such a negative voltage may be obtained, for example, by grounding first terminal 3t, while applying a positive unipolar voltage signal to second terminal 26t.

In general, the unipolar voltage signal applied to the terminals may have any suitable form, such as any of the forms described in US Patent Application Publication 2011/0301594, whose disclosure is incorporated herein by reference. For example, the unipolar voltage signal may be a periodic signal that includes a sequence of pulses, each of these pulses, for example, being shaped as the positive half-wave of a sinusoidal signal, or having a trapezoidal shape. Alternatively, the unipolar voltage signal may be a direct current (DC) voltage signal.

Although the amplitude of the unipolar voltage may have any suitable value, this amplitude is typically between 0.1 and 100 V, e.g., between 1 and 100 V, such as between 1 and 50 V, or between 4 and 40 V. Such an amplitude is large enough to be effective, yet small enough such as to avoid damaging the tissue near the thrombus. For example, as described in US Patent Application Publication 2011/0301594 with reference to FIG. 1D thereof, each trapezoidal pulse of the applied voltage signal may (i) linearly ramp up from ground level (0 volts) to an amplitude of around 40 volts, over a time period of around 5 milliseconds, (ii) remain constant over a time period of around 5 milliseconds, and then (iii) linearly ramp down to ground level over a time period of around 5 milliseconds. Before the beginning of the subsequent pulse, the voltage may remain at ground level for another time period of around 5 milliseconds. In general, the applied unipolar voltage signal, if pulsatile, may have any suitable frequency, such as between 0.1 Hz to 100 MHz, e.g., around 50 Hz, as in the example immediately above. Typically, the unipolar voltage is applied such that a current having an amplitude of between 0.1 and 4 mA (e.g., 1-3 mA) is passed between the first electrode and the second electrode.

In some embodiments, the voltage source that applies the unipolar voltage is current-regulated, e.g., to between 0.1 and 4 mA. In other embodiments, the voltage source is voltage-regulated, e.g., to between 1 and 50V. Typically, the voltage is applied for a duration of more than 1 second, to facilitate attachment of the thrombus to the first electrode, but less than 10 minutes, to prevent risk to the patient. For example, the duration may be more than 5 seconds but less than 5 minutes, e.g., more than 10 seconds but less than 2 minutes.

Typically, the unipolar voltage is applied while the first electrode is in contact with the thrombus, and while the second electrode is inside the body of the subject, e.g., within the catheter lumen, but not in contact with the thrombus. (Notwithstanding the above, it is noted that in some embodiments, e.g., as described below with reference to FIG. 4, both of the electrodes may contact the thrombus.) For example, prior to applying the unipolar voltage, the electrode assembly may be advanced, such that the first electrode pierces the thrombus (i.e., passes through the thrombus in contact therewith). Alternatively, as described below with reference to FIG. 3, catheter 20, with the two electrodes appropriately positioned within the catheter lumen, may be advanced through the thrombus and then withdrawn from over the first electrode, such that the first electrode is positioned within the thrombus.

In some cases, it may be advantageous for the position of the catheter to remain as distal as possible during the application of the unipolar voltage, to facilitate the collection of any bubbles or debris generated during the procedure. Hence, the second electrode, and even the first electrode and the thrombus with which it is in contact, may be partly or fully contained within the catheter lumen while the unipolar voltage is applied. For example, following, or together with, the advancement of the electrode assembly as described in the paragraph above, the catheter may also be advanced, such that the second electrode and/or the first electrode are contained with the catheter lumen during the subsequent application of the unipolar voltage.

Typically, while the unipolar voltage is applied, the respective distal tips of the electrodes are spaced apart from each other by a distance D1 of between 1 and 100 mm, such as between 2 and 30 mm. Such a distance facilitates suitable electrical conductivity between the electrodes via the blood at the treatment site, while maintaining the second electrode at a sufficient distance from the thrombus such as to prevent contact of the second electrode with the thrombus. Alternatively, distance D1 may be less than 1 mm (in which case the second electrode may contact the thrombus), or more than 100 mm.

In some embodiments, the separation distance L2 between the first electrode and the second electrode (i.e., the distance between the proximal tip of the first electrode and the distal tip of the second electrode) is relatively small, such as to reduce the amount of electric current that passes through the tissue surrounding the blood vessel in which the thrombus is located. For example, assuming the total diameter of (i) the blood vessel, and (ii) the tissue surrounding the blood vessel, is D2, such that the total transverse cross-sectional area A2 of the blood vessel and the surrounding tissue is $\pi*(D2/2)^2$, L2 may satisfy the relation $L2*(1\ mm) \ll A2$, where "$\ll$" implies "at least one order of magnitude smaller than." (The above assumes L2 is given in mm, and A2 in mm$^2$.) In some embodiments, L2 is even smaller, in that L2 satisfies the relation $L2*(1\ mm) \ll A1$, where A1 is the transverse cross-sectional area of the blood vessel.

In general, the ease of manufacture increases with L2. Hence, for ease of manufacture, embodiments of the present invention typically set L2 in accordance with the blood-vessel dimensions, rather than always making L2 as small as possible. In other words, for a relatively large blood vessel, since it may not be necessary to have such a small separation between the electrodes, a larger separation distance may be used, relative to a smaller blood vessel. Some embodiments of the present invention define a range of suitable separations for each particular application, where the upper limit of the range is one order of magnitude less than $A1/(1\ mm)$, and the lower limit of the range is two orders of magnitude smaller than $A1/(1\ mm)$.

For example, in neurovascular applications, a relatively large vessel may be around 6 mm in diameter, such that the vessel has a cross-sectional area of around 30 mm$^2$. Hence, for such application, distance L2 may be between 0.3 mm and 3 mm. Smaller vessels, such as in the more distal segments of the middle cerebral artery (MCA) in the brain, have a cross-sectional area of around 7 mm$^2$. Hence, for such applications, L2 may be between 0.07 mm and 0.7 mm. For the treatment of other conditions, such as deep vain thrombosis, pulmonary embolisms, or coronary artery occlusions, L2 may likewise be set in accordance with the blood-vessel diameter (or cross-sectional area), as described above.

Typically, the electrodes are made of different respective conductive metals. Typically, when performing a thrombectomy (by applying a positive voltage between the first and second electrodes), the first electrode has a higher electronegativity than that of the second electrode. For example, the first electrode may be made of gold or platinum, with the second electrode made of titanium or stainless steel. Conversely, when performing thrombus dissolution (by applying a negative voltage between the first and second electrodes), the first electrode typically has a lower electronegativity than that of the second electrode.

(It is noted that, in the context of the present description and claims, an electrode may be considered to be "made of" a particular material, even if it is only coated by this material. For example, an electrode "made of" titanium may comprise any suitable material that is coated by a layer of titanium.)

In some embodiments, apparatus 21 comprises radiopaque markers, which facilitate visualization of the apparatus using x-ray imaging. For example, one or more radiopaque gold rings or coatings may cover a portion of the second electrode, if the second electrode is made of titanium, or any other material that is generally not radiopaque.

In some embodiments, apparatus 21 comprises a balloon, disposed proximally to the first electrode. Prior to the first electrode contacting the thrombus, the balloon is inflated, such as to center the first electrode relative to the thrombus. The first electrode may then pass through the center of the thrombus, thus increasing the effectiveness of the subsequently applied unipolar voltage.

Reference is now made to FIG. 2, which is a schematic illustration of electrode assembly 23, in accordance with some embodiments of the present invention.

In some embodiments, as shown in FIG. 2, electrode assembly 23 comprises a (hollow) tube 28, second electrode 26 being shaped to define part of the wall of tube 28. (Tube 28 may alternatively be referred to as a "hollow shaft.") As further shown, first electrode 3 may be disposed at the distal end of the tube. As described above with reference to FIG. 1, first electrode 3 may comprise a straight wire (that is not hollow), having any suitable diameter and length. For example, the diameter d1 of the first electrode may be between 0.01 and 4 mm, and/or the length L1 of the first electrode may be between 0.1 and 50 mm (e.g., between 5 and 25 mm). In some embodiments, as shown, the diameter of tube 28 is the same as the diameter of the first electrode.

For example, tube 28 may comprise a proximal portion 34, made of any suitable conductive or non-conductive material, and a distal portion 36, comprising a tubular second electrode 26, along with an electrical insulator 32, which typically is also tubular, that separates the second electrode from the first electrode. A first wire 5a, which passes through the lumen of the tube, may be connected at its distal end to the first electrode. Likewise, a second wire 5b, also passing through the lumen of the tube, may be connected at its distal end to the second electrode. In such embodiments, a voltage source 46 may apply a unipolar voltage between the electrodes by applying the unipolar voltage between first wire 5a and second wire 5b.

Alternatively, in place of proximal portion 34 of the tube wall, second electrode 26 may extend to the proximal end of the tube. In such embodiments, second wire 5b may not be needed. Rather, a unipolar voltage may be applied between the electrodes by applying the unipolar voltage between first wire 5a and second electrode 26 directly, or between first wire 5a and an external wire connected to second electrode 26.

In general, the distance D1 between the respective distal tips of the electrodes may have any suitable value. Typically, however, distance D1 is between 1 and 100 mm, such as between 2 and 30 mm, as described above with reference to FIG. 1. For example, if L1 is 15 mm, the length of insulator 32 may likewise be 15 mm, such that D1 is 30 mm. Likewise, separation distance L2 (which is equivalent to the length of insulator 32) may be relatively small, and may be set in accordance to the dimensions of the blood vessel in which the thrombus is contained, as described above with reference to FIG. 1.

Insulator 32 may be made of any suitable biocompatible insulating material, such as Polyimide, Silicone, PolyUrethane, PolyEthylene, or Teflon. In some embodiments, insulator 32 comprises a glue or adhesive, such as a cyanoacrylate adhesive. In other embodiments, instead of insulator 32, an air gap (of length L2) separates the two electrodes from one another.

Reference is now made to FIG. 3, which is a schematic illustration of electrode assembly 23, in accordance with other embodiments of the present invention.

In FIG. 3, as in FIG. 2, second electrode 26 is tubular, and is coaxial with first electrode 3, in that the two electrodes share a common longitudinal axis 27. FIG. 3 differs from FIG. 2, however, in that first electrode 3 passes through the lumen of second electrode 26. In particular, first electrode 3 passes through the lumen of tubular insulator 32, which in turn passes through the lumen of second electrode 26. Insulator 32 is thus disposed proximally to the exposed portion of the first electrode, and the second electrode, in turn, is disposed proximally to the exposed portion of the insulator.

In some embodiments, first electrode 3, tubular insulator 32, and second electrode 26 are fixed in place, relative to each other. In other embodiments, at least one of these elements is slideable with respect to the others. For example, the first electrode may be slideable within the tubular insulator, and/or the second electrode may be slideable over the tubular insulator. Thus, for example, prior to applying the unipolar voltage, the second electrode may be advanced over the insulator, until the distance D1 between the respective distal tips of the electrodes is less than a predefined target (such as 100 mm or 30 mm, as described above with reference to FIG. 1), and/or until the distance between the two electrodes (i.e., the exposed length of insulator 32) is less than a predefined target separation distance L2 (such as 3 mm or 0.7 mm). Alternatively or additionally, prior to applying the unipolar voltage, the first electrode may be advanced through the lumen of the insulator, until the length between the respective distal tips of the electrodes reaches a predefined target, and/or until the distance between the two electrodes reaches a predefined target.

In some embodiments, second electrode 26 is shaped to define only the distal portion of the wall of tube 28 (i.e., the second electrode does not extend to the proximal end of tube 28), and is therefore connected to the proximal end of electrode assembly 23 via a wire, as in FIG. 2. Alternatively or additionally, first electrode 3 may not extend to the proximal end of the electrode assembly; rather, a wire, passing through the lumen of insulator 32, may connect the first electrode 3 to the proximal end of electrode assembly, as in FIG. 2.

In some embodiments, the exposed portion of the first electrode is straight, as shown in FIG. 3. In other embodiments, the exposed portion of the first electrode is curved, such as to decrease the likelihood that the electrode will damage tissue of the subject.

As described above with reference to FIG. 1, radiopaque markers may be disposed at any suitable location on electrode assembly 23. For example, FIG. 3 shows an embodiment in which the distal portion of the second electrode comprises a radiopaque marker 38, comprising a ring of radiopaque material.

In some embodiments, a second tube, concentric with tube 28, is disposed within, or around the outside surface of, tube 28. Such a second tube may be radiopaque, thus facilitating visibility of the electrode assembly under fluoroscopy, and/or may impart particular mechanical properties (e.g., rigidity) to the electrode assembly.

Reference is now made to FIGS. 1-3, collectively.

Typically, prior to applying the unipolar voltage for thrombectomy or thrombus dissolution, the first electrode is advanced through the thrombus, at least until the thrombus contacts the electrical insulator (e.g., insulator 32) that is disposed proximally to the exposed portion of the first electrode. For example, the first electrode may be advanced through the thrombus until the entire length of the first electrode (or the entire length of the exposed portion of the first electrode) contacts the thrombus. This increases the effect of the applied voltage, by reducing, or eliminating, any exposed portion of the first electrode that is proximal to the thrombus. The first electrode may be advanced through the thrombus by distally pushing the entire electrode assembly through the lumen of catheter 20; alternatively, for embodiments in which the first electrode is slideable with respect to other elements belonging to the electrode assembly, the first electrode may be pushed, while holding the remainder of the electrode assembly in place.

Although the thrombectomy or thrombus-dissolution procedure described herein is, typically, performed under fluoroscopy, it may be difficult, based on fluoroscopy alone, to ascertain that the thrombus has contacted the insulator. Hence, in some embodiments, the impedance between the first electrode and the second electrode is measured as the first electrode is advanced through the thrombus, as this measured impedance indicates the extent to which the first electrode is exposed proximally to the thrombus. (The impedance increases as more of the electrode becomes covered by the thrombus.) Based on the measured impedance, it may be ascertained that the thrombus has contacted the insulator.

In some embodiments, to measure the impedance, a voltage, which is lower than the unipolar voltage applied for treatment, is applied between the electrodes, and the resulting current is then measured. The impedance is then the voltage divided by the measured current. (Since the actual value of the impedance is not necessarily of interest, the impedance may be "measured" by measuring the current, even without computing the actual impedance value. For example, once the current reaches a minimum, it may be ascertained that the thrombus has contacted the insulator, even without computing any impedance values.) In other embodiments, the impedance is measured by passing a low current between the electrodes, and then measuring the resulting voltage.

In other embodiments, catheter 20, while containing the two electrodes, is advanced through the thrombus. Subsequently, the catheter is withdrawn from over the first electrode (and, optionally, from over the second electrode), such that the first electrode remains positioned within the thrombus, with the second electrode being positioned proximally thereto. Subsequently, the unipolar voltage is applied.

Figure 4:
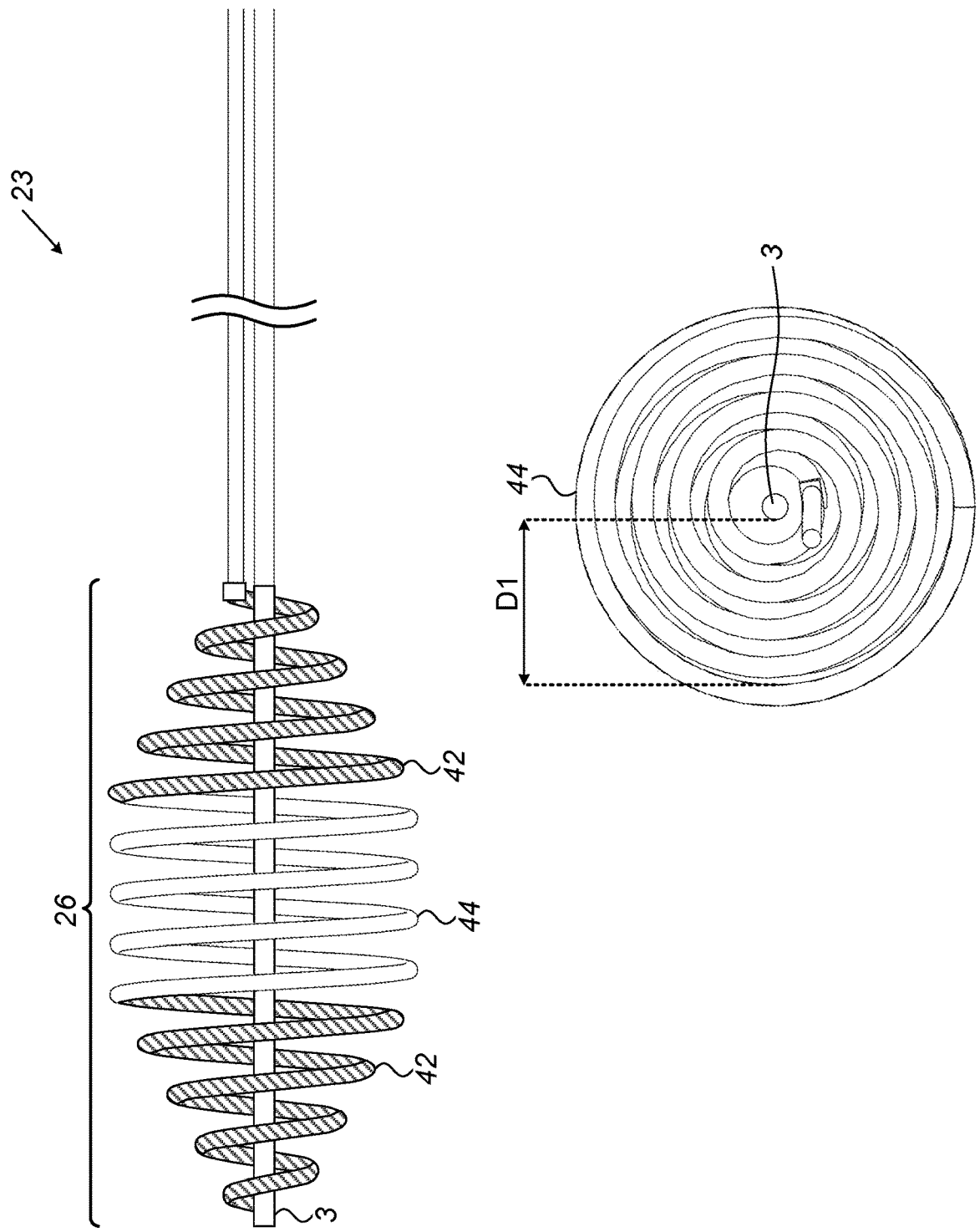

Reference is now made to FIG. 4, which is a schematic illustration of electrode assembly 23, in accordance with yet other embodiments of the present invention.

In some embodiments, second electrode 26 wraps around first electrode 3, with a radial gap separating between the two electrodes. For example, second electrode 26 may be shaped to define a helix, and first electrode 3, which is typically rod-shaped, may pass through the second electrode, along the longitudinal axis of the second electrode. Typically, in such embodiments, the proximal and distal portions of the second electrode are covered by an insulating cover 42, such that only the middle portion 44 of the second electrode is exposed. (Middle portion 44 includes the portion of the second electrode having a maximum radius, relative to other portions of the second electrode.) Insulating cover 42 helps prevent unwanted electrical contact between the two electrodes. (In these embodiments, the first electrode may be referred to as an "inner electrode," and the second electrode may be referred to as an "outer electrode," or as a "stent.")

Typically, the first electrode passes through the center of the second electrode, such that the distance D1 between the first electrode and middle portion 44, which is approximately equal to the radius of middle portion 44, is between 1 and 100 mm, such as between 2 and 30 mm. Alternatively, distance D1 may have any other suitable value.

Typically, the second electrode is expandable. Prior to applying the unipolar voltage, catheter 20 (FIG. 1), which contains both the first electrode, and the second electrode in a crimped position, is advanced through the thrombus. Subsequently, the catheter is withdrawn from over the two electrodes, such that the second electrode expands, from the crimped position, within the thrombus. Subsequently, a positive unipolar voltage is applied between the first and second electrodes, causing the thrombus to become attached to the first electrode. During the application of the voltage, the first electrode may protrude distally from the second electrode. Alternatively, the distal end of the first electrode may remain inside of the second electrode.

During, and/or following, the application of the unipolar voltage, the electrode assembly is withdrawn. During withdrawal of the electrode assembly, the second electrode, which is positioned within the thrombus, helps remove the thrombus, by applying, to the thrombus, a mechanical force that complements the attractive force between the thrombus and the first electrode.

For any of the configurations described above with reference to FIGS. 1-4, a negative unipolar voltage may be applied between the first and second electrodes, causing the thrombus to dissolve. In yet other embodiments, an alternating voltage, instead of a unipolar voltage, may be applied, to cause thermal coagulation.

Although FIGS. 1-4 show embodiments in which the two electrodes are coaxial with one another, in that they share a common longitudinal axis (as explicitly indicated in FIG. 3), it is noted that other embodiments are also within the scope of the present invention. For example, as described in US Patent Application Publication 2011/0301594 with reference to FIGS. 1A-C thereof, the two electrodes may pass through separate lumens of catheter 20, or may pass, side by side (but separated by an insulator), through a common lumen of catheter 20.

It is noted that any of the tubes and catheters described herein may comprise a wall that is at least partly solid, coiled, braided, or meshed. Likewise, any of the electrodes described herein may be shaped to define a tube, a coil (which may have a constant or variable pitch), a braid, or a mesh.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. Apparatus for removal of a thrombus from a body of a subject, the apparatus comprising:
   an inner electrode;
   an outer electrode, configured to wrap around the inner electrode; and
   a discontinuous electrically-insulating cover disposed between the inner electrode and the outer electrode,
      the inner electrode being configured to lie radially opposite the outer electrode at a break in the discontinuous electrically-insulating cover such that, when a voltage is applied between the inner electrode and the outer electrode, an electric current passes between the inner electrode and the outer electrode via the break.

2. The apparatus according to claim 1, wherein an electronegativity of the inner electrode is greater than an electronegativity of the outer electrode.

3. The apparatus according to claim 1, wherein the outer electrode is configured to wrap around the inner electrode such that, when the inner electrode passes through a center of the outer electrode, a radial distance between the inner electrode and the outer electrode at the break is between 1 and 100 mm.

4. The apparatus according to claim 3, wherein the outer electrode is configured to wrap around the inner electrode such that, when the inner electrode passes through the center of the outer electrode, the radial distance is between 2 and 30 mm.

5. The apparatus according to claim 1, wherein the outer electrode is shaped to define a helix.

6. The apparatus according to claim 1, wherein a diameter of the inner electrode is between 0.01 and 4 mm.

7. The apparatus according to claim 1, wherein the discontinuous electrically-insulating cover covers a proximal portion of the outer electrode and a distal portion of the outer electrode but does not cover a middle portion of the outer electrode, and wherein a radius of the middle portion of the outer electrode is greater than that of the proximal portion of the outer electrode and greater than that of the distal portion of the outer electrode.

8. The apparatus according to claim 1, wherein the inner electrode passes through a center of the outer electrode.

9. The apparatus according to claim 1, wherein the inner electrode is slidable with respect to the outer electrode.

10. A method, comprising:
applying a voltage between an inner electrode, which includes an inner exposed portion that extends along a longitudinal axis, and an outer electrode, which includes an outer exposed portion that extends along the longitudinal axis, while the inner electrode is in contact with a thrombus in a body of a subject and is positioned within the outer electrode such that the inner exposed portion is radially opposite the outer exposed portion and an insulating cover insulates another portion of the outer electrode from another portion of the inner electrode around which the other portion of the outer electrode is wrapped,
thereby causing the inner electrode to attach to the thrombus; and
subsequently, removing the thrombus from the body of the subject by withdrawing the inner electrode from the body.

11. The method according to claim 10, wherein an electronegativity of the inner electrode is greater than an electronegativity of the outer electrode.

12. The method according to claim 10, further comprising, prior to applying the voltage, advancing the inner electrode through the thrombus until an entire length of the inner exposed portion contacts the thrombus.

13. The method according to claim 10, wherein an amplitude of the voltage is between 1 and 100 V.

14. The method according to claim 10, wherein applying the voltage comprises applying the voltage such that a current having an amplitude of between 0.1 and 4 mA is passed between the inner electrode and the outer electrode.

15. The method according to claim 10, wherein applying the voltage comprises applying the voltage while a radial distance between the inner exposed portion and the outer exposed portion is between 1 and 100 mm.

16. The method according to claim 15, wherein applying the voltage comprises applying the voltage while the radial distance is less than 3 mm.

17. The method according to claim 10, wherein the outer electrode is expandable, and wherein the method further comprises, prior to applying the voltage:
advancing a catheter, containing both the inner electrode, and the outer electrode in a crimped position, through the thrombus; and
subsequently, withdrawing the catheter, such that the outer electrode expands, from the crimped position, within the thrombus.

18. The method according to claim 10, further comprising, prior to contacting the thrombus with the inner electrode, centering the inner electrode with respect to the thrombus, by inflating a balloon that is proximal to the inner electrode.

19. The method according to claim 10, wherein applying the voltage comprises applying the voltage for an interval of at least one second, and wherein the voltage is positive for at least 80% of the interval.

20. The method according to claim 10, wherein the outer exposed portion is at a middle of the outer electrode, and wherein the insulating cover insulates both a proximal portion of the outer electrode, which is proximal to the outer exposed portion, and a distal portion of the outer electrode, which is distal to the outer exposed portion, from the inner electrode.

21. A method, comprising:
applying a voltage between a first electrode, which is in contact with a thrombus in a body of a subject, and a second electrode, which is inside the body of the subject, for an interval of at least one second, the voltage being positive for at least 80% of the interval; and
subsequently to the thrombus becoming attached to the first electrode due to the voltage, removing the thrombus from the body of the subject.

* * * * *